United States Patent [19]

Earle

[11] Patent Number: 5,540,588

[45] Date of Patent: Jul. 30, 1996

[54] TEFLON-COATED INTRAORAL TISSUE RETRACTION CORD

[76] Inventor: Jeffrey O. Earle, 106 Haven Lake Ave., Milford, Del. 19963

[21] Appl. No.: 334,030

[22] Filed: Nov. 2, 1994

[51] Int. Cl.$^6$ .................................................. A61C 5/14
[52] U.S. Cl. ........................................................ 433/136
[58] Field of Search ................................... 433/136, 138, 433/140; 132/321

[56] References Cited

U.S. PATENT DOCUMENTS

| | | | |
|---|---|---|---|
| 4,321,038 | 3/1982 | Porteous | 433/136 |
| 4,483,675 | 11/1984 | Marshall | 433/141 |
| 4,871,311 | 10/1989 | Hagne | 433/136 |
| 4,892,482 | 1/1990 | Lococo | 433/136 |
| 5,032,445 | 7/1991 | Scantlebury et al. | 428/158 |
| 5,033,488 | 7/1991 | Curtis et al. | 132/321 |
| 5,039,303 | 8/1991 | Irwin | 433/24 |
| 5,063,948 | 11/1991 | Lloyd | 132/321 |
| 5,104,317 | 4/1992 | Riazi | 433/136 |
| 5,220,932 | 6/1993 | Blass | 132/321 |
| 5,305,768 | 4/1994 | Gross et al. | 132/321 |

FOREIGN PATENT DOCUMENTS 3122834  12/1982  Germany .......................... 433/136

OTHER PUBLICATIONS

"Actisite (Tetracycline Hydrochloride) Peridontal Fiber" by Procter & Gamble and Alza Corp. (Apr. 1994).
"Biological Therapies in Dentistry" a Bimonthly Newsletter for Dental Professionals, vol, 10, (Jul. 1994).
"Actisite (Tetracycline Hydrochloride) Peridontal Fiber" Bibliography (Jul. 1994).
"6–Month Multi–Center Evaluation of Adjunctive Tetracyline Fiber Therapy used in Conjunction with Scaling and Root Planing in Maintenance Patient: Clinical Results" by Michael G. Newman et al. (Jul. 1994).
"Serum Levels of Tetracyline During Treatment with Tetracycline–Containing Fibers" by John W. Rapley et al, (Oct. 1992).
"Zero–Order Delivery with Periodontal Placement of Tetracycline–Loaded Ethylene Vinyl Acetate Fibers" by M. Tonetti et al, (Feb. 15, 1990).
"Gore–Tex™Regenerative Material" By Gore Regenerative Technologies, 1994.
Clinical Research Associates Newsletter, vol. 15, Issue 6, Jun. 1991.
"Gore–Tex™Augmentation Material Patient Information" by W. L. Gore & Associates 1992.
"Your Choice, Gore–Tex®Periodontal Material for Guided Tissue Regeneration", by. W. L. Gore & Asso., Inc. 1987.
"Gore–Tex™Augmentation Material" by W. L. Gore and Assoc., Inc., 1991.
"Gore–Tex™Perodontal Material" by W. L. Gore & Assoc., 1991.

*Primary Examiner*—Cary E. O'Connor
*Attorney, Agent, or Firm*—Myers, Liniak & Berenato

[57] ABSTRACT

A dental retraction cord (or tape) for placement between a tooth and its adjacent gum tissue during dental impression taking and restorative procedures includes a thermoplastic material such as polytetrafluoroethylene (i.e. PTFE or Teflon) so that the cord is resistant to shredding, tearing, and sticking to dental restorative and impression taking materials. Additionally, chemical treatment of the cord may be avoided so as to reduce the risk of harmful side effects in chemically sensitive patients.

15 Claims, 2 Drawing Sheets

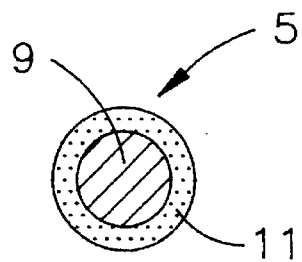
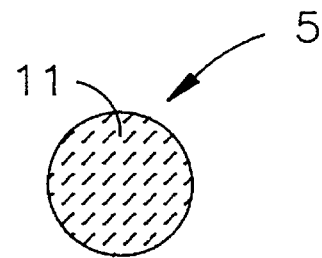
Fig. 2(a)  Fig. 2(b)
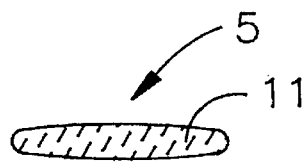
Fig. 3
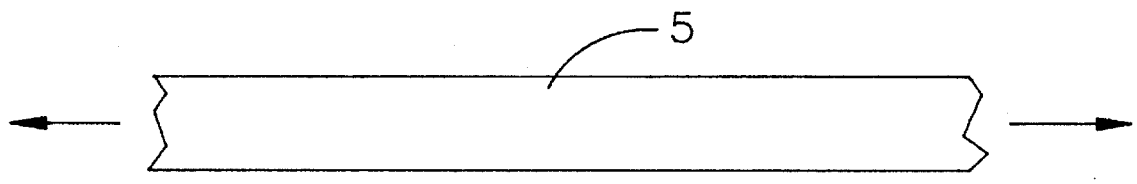
Fig. 4
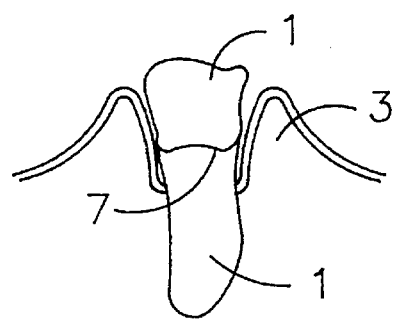
Fig. 5

TEFLON-COATED INTRAORAL TISSUE RETRACTION CORD

This invention relates to an intraoral dental retraction cord or tape and method for making same. More particularly, this invention relates to a gingival retraction cord which is resistant to shredding, tearing, and attachment to dental restorative and impression taking materials, the cord including a thermoplastic material (e.g. Teflon).

BACKGROUND OF THE INVENTION

Current dental practices make use of intraoral dental retraction cords during both restorative and impression taking operations (i.e. prosthetic dentistry). Such cords are often referred to as gingival tissue retraction cords.

When restoration of dental caries (cavities) at, near, or below the marginal attached gingiva (gumline) is required, dentists typically distend and retract the gingival or periodontal sulcus (eyelid-like space below the top of the gumline) in order to achieve sufficient access to the carious lesion. Thereafter, the practitioner generally removes the dental caries by drilling and fills the cleaned out hole in the tooth by way of a VLC composite resin or amalgam.

The distention of the periodontal sulcus is typically achieved by way of a rubber dam and corresponding clamp. Alternatively a conventional woven or braided gingival retraction cord is used. A significant drawback associated with the use of a rubber dam and corresponding clamp(s) is that they often produce periodontal tissue trauma and bleeding which compromise the restorative result. The problems which arise within respect to the use of conventional woven or braided cords is discussed below.

Prosthetic dentistry is known in the art to involve the construction of crowns, caps, partial dentures, full dentures, implants, and fixed bridgework. The practice of prosthetic dentistry often requires the taking of accurate impressions (or molds) of a particular tooth, teeth, or implant for which prosthetics will be fabricated at a dental laboratory. At the interface (or limit line) of the tooth (or root, or implant) surface to be worked on and the gingival margin (gumline), it is important that prior to impression taking, the gingival sulcus be reflected or retracted in order to register an accurate impression of the prepared tooth (or root, or implant) structure.

This type of refraction is typically accomplished by way of conventional dental periodontal sulcular retraction cord (or gingival retraction cord). In short, a small diameter (e.g. 1–2 mm dia.) braided or woven cotton cord is pressed into the periodontal sulcus prior to flowing the impression material onto the tooth, teeth, or implant. Conventional retraction cord is often impregnated with certain chemicals (e.g. racemic epinephrine, aluminum choride, or adrenalin).

In use, this conventional retraction cord is typically unwound from a spool or withdrawn from a container. The dental practitioner estimates the length of cord required for the particular application and snips the desired length of cord from the spool. The practitioner then wraps the cord around the tooth and either ties a knot to hold the cord in position on the cervical portion of the tooth, or overlays several turns of the cord on the tooth to hold the cord in place. The practitioner then packs the cord into the gingival sulcus so as to reflect or retract the gum tissue away from the tooth structure thereby enabling the accurate taking of an impression of the tooth inclusive of its cervical portion in prosthetic dentistry for example.

Practitioners often use small conventional dental instruments to position the cord in the periodontal space. Once the impression material hardens and is removed from the tooth and mouth or the filling is in place, the retraction cord is removed from the periodontal space and discarded. It is noted that the "periodontal space," "periodontal sulcus," "marginal periodontal tissue," and "gingival sulcus" are synonymous terms well-known in the art, and their well-known meaning is adopted here.

Problems arise in the use of these woven or braided cords whether used in the process of drilling and filling dental caries or in the other processes discussed above. For example, it is often the case that the insertion and removal of conventional woven or braided string-like gingival retraction cord produces gingival tissue trauma and periodontal sulcular bleeding thereby compromising the accuracy of the impression or filling and causing post operative discomfort to the patient. Furthermore, some patients are chemically sensitive to conventional chemically impregnated retraction cords and experience discomforting side effects as a result thereof.

Another problem associated with conventional woven or braided string-like dental retraction cords is their tendency to physically attach or stick to dental restorative and impression taking materials. When such sticking occurs, it becomes extremely difficult for the practitioner to remove the cord from both the periodontal sulcus and the finished restoration and/or impression taking material.

Yet another problem with conventional string-like woven or braided retraction cords is their tendency to shred or tear during both insertion and removal from the periodontal sulcus. Such shredding and tearing often produces undesirable gingival sulcular tissue trauma, bleeding, and post operative patient discomfort. Additionally, torn or shredded pieces of the cord may be left behind inside the patient's mouth or gumline leading to the possibility of infection.

U.S. Pat. No. 4,892,482 discloses a gingival tissue dental retraction cord made of a plurality of strands including a central stiffener strand of, for example, copper wire or other material which provides the cord with deformability. Unfortunately, the construction of the dental retraction cord of this patent renders it subject to the above-mentioned disadvantages associated with other conventional retraction cords.

U.S. Pat. No. 4,871,311 discloses a dental retraction cord for uncovering and draining the preparation limit line of a tooth where the tooth emerges from the gum tissue during dental procedures such as the taking of dental impressions, the cementing of crowns, and the performance of conservative caries therapy (i.e. the type uses contemplated herein by the subject invention). The retraction cord of this patent, after being inserted into the periodonal sulcus, swells and thereby mechanically uncovers the preparation limit line and tends to stop bleeding of the gum tissue. The preferred material for making the swelling cord of this patent is a super absorbent swelling material made of an acrylic fiber having a skin constituted by a co-polymer of polyacrylic acid and polyammonium acrylate and a core of polyacrylonitrile, in which the skin provides about thirty percent of the weight of the fiber. Unfortunately, the cord of this patent, both before and after swelling, is susceptible to the disadvantages and problems set forth above.

U.S. Pat. No. 4,321,038 discloses a braided gingival retraction cord which is subject to the above-described disadvantages. The cord of this patent includes strands of fluid absorbent yarns or thread, such as cotton. Following fabrication, the braided cord of U.S. Pat. No. 4,321,038 is passed through a chemically impregnating solution containing a concentration of such chemicals as epinephrine, alum, aluminum chloride, or mixtures thereof, to saturate the cord.

U.S. Pat. No. 5,033,488 discloses a porous, high strength dental floss made of expanded polytetrafluoroethylene (i.e. PTFE or "Teflon™"). The dental floss of this patent, coated with microcrystalline wax, is made using expanded PTFE (Teflon) so as to allow the dental floss to pass smoothly through the narrow spaces defined between adjacent teeth.

It is also known to use PTFE in clinical dentistry for periodontal regeneration surgical procedures. For example, GORE-TEX™ e-PTFE is often applied to periodontal osseous defects such as those which can occur around molar teeth or endosseous implants. Such material is used to guide regeneration of new bone around teeth or dental implants.

This GORE-TEX™ material is also used for guided tissue regeneration by draping the material over a surgically exposed tooth and cleansed peridontal site (e.g. a Class I furcation defect) so as to allow for regrowth of healthy periodontal tissue. Periodontal regeneration often occurs in this space. After removal of the PTFE material, newly regenerated periodontal fibers provide additional tooth support. These uses of e-PTFE, however, are not related to gingival retraction cord.

It is apparent from the above that there exists a need in the art for a dental retraction cord or tape which (1) is resistant to shredding and tearing; (2) is resistant to sticking to dental restorative and impression taking materials; and (3) reduces tissue trauma, bleeding, and post operative patient discomfort. Furthermore, a need arises in the art for a dental retraction cord free of chemical impregnation so as to permit the cord to be used during dental procedures carried out upon chemically sensitive patients.

It is the purpose of this invention to fulfill the above-described needs in the art, as well as other needs which will become apparent to the skilled artisan from the following detailed description of this invention.

SUMMARY OF THE INVENTION

Generally speaking, this invention fulfills the above-described needs in the art by providing a dental retraction cord or tape of a predetermined size and shape so as to be placeable between a tooth and its adjacent gum tissue thereby to properly retract the gum tissue from the tooth a predetermined distance, the cord being comprised of a substantially non-toxic material in an amount sufficient and of a cross-sectional size and shape sufficient to retract gum tissue said material being resistant to tearing, shredding and sticking to dental restorative and impression taking materials.

In certain preferred embodiments of this invention, the thermoplastic material is polytetrafluoroethylene (known in the art as "Teflon").

In certain further preferred embodiments of this invention the cord has an outer diameter of from about 1.0–2.0 mm.

This invention further fulfills the above-described needs in the art by providing a dental retraction cord for insertion into the periodontal sulcus between a tooth and its adjacent gum tissue so as to (1) achieve sufficient access to dental caries at, near, or below the gumline; or (2) retract the gingival sulcus prior to and during impression taking procedures for crowns, caps, bridges, dentures, implants, and the like, the dental retraction cord comprising:

an elongated body for insertion into the periodontal sulcus, the elongated body including a smooth outer surface resistant to shredding, tearing, and adhesion to dental restorative and impression taking materials.

In certain preferred embodiments of this invention, the smooth outer surface of the elongated body includes a non-sticking material such as expanded polytetrafluoroethylene (i.e. expanded Teflon).

This invention further fulfills the above-described needs in the art by providing a method of making a dental retraction cord or tape for insertion into the periodontal sulcus between a tooth and its adjacent gum, the method comprising the steps of:

(a) forming an elongated body for insertion into the periodontal sulcus; and (b) including a non-sticking material in the elongated body so that the body is resistant to tearing, shredding, and sticking to dental materials.

This invention will now be described with respect to certain embodiments thereof, accompanied by certain illustrations, wherein:

IN THE DRAWINGS

Figure 1A:
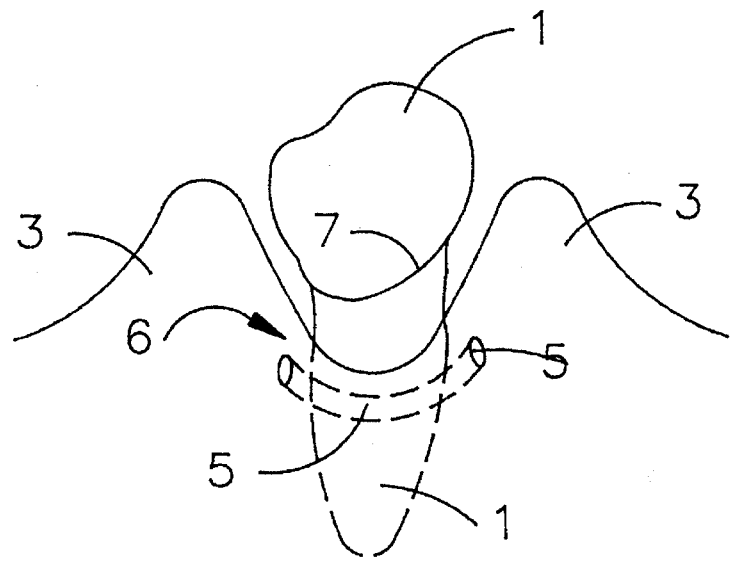
FIG. 1(a) is a front elevational view of a tooth and its adjacent gum tissue, wherein retraction cord according to an embodiment of this invention is disposed in the periodontal sulcus so as to retract the gum tissue from the tooth surface.

FIGS. 2(a)–2(b) are cross-sectional views of dental retraction cord according to certain embodiments of this invention.

FIG. 3 is a cross-sectional view of a dental retraction tape according to an embodiment of this invention.

FIG. 4 is a side elevational view illustrating the elongated body of the dental retraction cord or tape according to certain embodiments of this invention.

FIG. 5 is a cross-sectional side view of a tooth and its adjacent gum in a non-retracted state.

DETAILED DESCRIPTION OF CERTAIN EMBODIMENTS OF THIS INVENTION

Referring now more particularly to the accompanying drawings in which like reference numerals indicate like parts throughout the several views.

Retraction cord or tape 5 as shown in FIGS. 1–4 is made so as to include a non-toxic material such as polytetrafluoroethylene (known in the art as PTFE or "Teflon"). The inclusion of the non-toxic material (e.g. Teflon) in flexible retraction cord 5 results in the cord being resistant to sticking or adhering to dental materials (e.g. restorative and/or impression taking materials). Additionally, the presence of the non-toxic thermoplastic material within cord 5 renders the cord resistant to shredding and tearing during its insertion and removal from periodontal sulcus 6 and therefore reduces tissue trauma, bleeding, and post operative patient discomfort. PTFE and/or expanded PTFE, which may be provided in cord 5, are biocompatible in the human body, causing no known clinical or scientific adverse medical reactions. PTFE materials are commercially available from, for example, DuPont.

Retraction cord 5 including the non-toxic material may be placed between tooth 1 and its adjacent gumline 3 by way of conventional techniques and tools used for placement of conventional gingival retraction cord. Cord 5 may also be removed easily following prosthetic impression or restorative procedures by conventional methods known in the art.

Furthermore, the presence of the non-toxic PTFE material allows cord 5 to be made (if desired) without the presence of chemically impregnated additives such as aluminum chloride, racemie epinephrine, alum, etc. Thus, cord 5 may be used on chemically sensitive patients and their previously experienced adverse chemical side effects caused by chemically impregnated cords can be avoided.

The provision of the non-sticking and non-toxic material (e.g. Teflon) in cord 5 causes the cord to have a smooth outer or contacting surface in certain embodiments of this invention. The smooth outer surface of cord 5 is an improvement over the non-smooth outer surfaces of prior art woven or braided cords (e.g. made from cotton) which are subject to tearing, shredding, and causing patient discomfort.

FIG. 1(a) is a front elevational view of tooth 1 and its adjacent gum tissue 3. Retraction cord 5 according to an embodiment of this invention is shown disposed within periodontal sulcus 6, or in other words within the periodontal space between tooth 1 and its adjacent gum tissue 3. The disposition of dental retraction cord 5 in periodontal sulcus 6 reflects or retracts gum tissue 3 from the tooth structure to be worked on so as to ensure adequate visibility of and access to the surface of tooth 1.

For instance, in prosthetic dentistry when taking tooth impressions in preparing for a crown or the like, tooth 1 including its preparation limit line 7 must remain clear of fluid and humidity. Additionally, limit line 7 must remain uncovered and accessible. FIG. 5 illustrates a tooth 1 in unretracted form with gum 3 closely adjacent tooth 1.

Figure 1B:
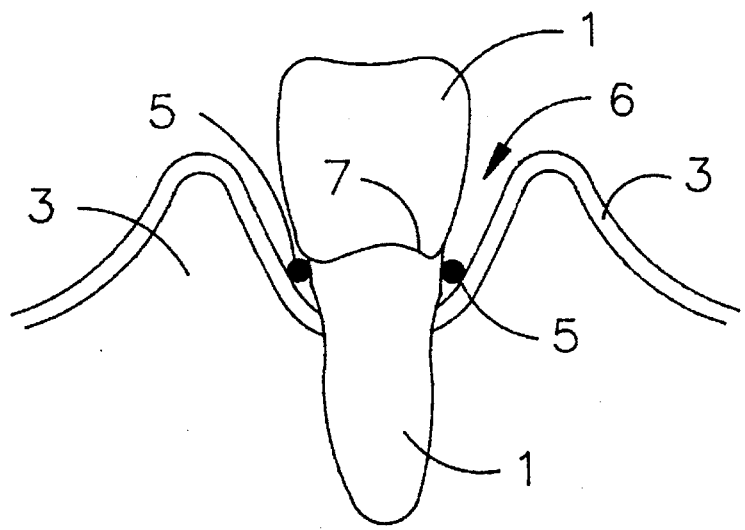
FIG. 1(b) is a cross-sectional side view of the retraction cord according to the FIG. 1(a) embodiment of this invention, wherein the cord is positioned in the peridonal sulcus between a tooth and its adjacent gum tissue so as to reflect or retract the gum tissue from the tooth surface.

In order to uncover preparation limit line 7, flexible or limp-like retraction cord 5 as shown in FIGS. 1(a) and 1(b) is pressed into periodontal sulcus 6 surrounding tooth 1 by way of a conventional dental instrument, for example. In other words, cord or tape 5 is disposed within the gingival crevice between tooth 1 and gum tissue 3. The disposition of cord 5 within periodontal sulcus 6 allows limit line 7 to remain uncovered, accessible, and substantially free of bodily fluids.

Retraction cord 5 may be utilized by practitioners (e.g. dentists) as illustrated in FIGS. 1(a) and 1(b) in both prosthetic and restorative dentistry. In restorative dentistry, for example, when restoration of dental caries at, near, or below the marginal attached gingiva (i.e. gumline) is required, it is necessary to distend and retract the adjacent gum tissue 3 in order to achieve adequate access to the carious lesion. Such access allows successful removal of caries and placement of fillings (e.g. VLC composite resins or amalgams).

Retraction cord 5 may also be used in prosthetic dentistry involving the construction of crowns, caps, bridge works, dentures, implants, and the like. In prosthetic dentistry, it is imperative that accurate impressions or molds of a tooth, teeth, or implant be obtained for which prosthetics will subsequently be fabricated at a dental laboratory. At the interface of the tooth surface and the gingival margin (i.e. gumline), it is important prior to impression taking that the gingival sulcus be retracted so that an accurate impression of the prepared tooth structure can be made. This is accomplished by packing retraction cord 5 in periodontal sulcus 6 between tooth 1 and gum 3 prior to flowing impression taking material onto the tooth or teeth. This is shown in FIGS. 1(a)–1(b). Once the impression material hardens and is removed from the patient's mouth, retraction cord 5 may be removed from the periodontal sulcus and discarded.

FIGS. 2(a) and 2(b) are cross-sectional views of retraction cord 5. FIGS. 2(a) and 2(b) illustrate a substantially circular or cord-like structure, while FIG. 3 illustrates a tape-like structure.

As shown in FIG. 2(a), retraction cord 5 according to this particular embodiment may be made of a braided or woven central core 9 coated around its substantial or entire outer periphery with non-sticking and non-toxic thermoplastic material 11. Thermoplastic material 11 may, for example, be polytetrafluoroethylene (PTFE) or expanded polytetrafluoroethylene (e-PTFE) in certain embodiments of this invention. Additionally, conventional thermoplastic and thermosetting materials other than PTFE which provide similar results may instead be used as coating 11. Thus, a cord with a smooth or substantially smooth outer surface is provided in this embodiment (as well as in other embodiments).

Central core 9 of retraction cord 5 as shown in FIG. 2(a) may be made of conventional woven or braided retraction cord which is simply coated with thermoplastic material 11. For example, core 9 may be made of a braided or woven string-like twine or cord made of any conventional material such as cotton. The overall diameter of cord 5 may be from about 0.5–3.0 mm, more preferably from about 0.5–2.5 mm, and most preferably from about 1.0–2.0 mm. The overall elongated length of cord 5 is unlimited and may be determined in accordance with packing and winding requirements or restrictions. Cord 5 may be wound on a spool and packaged in a dispensing container.

Thus, according to the FIG. 2(a) embodiment, typical cotton strands may be woven or braided together and then be coated with PTFE by way of, for example, a conventional die/extruder device.

As shown in the FIG. 2(b) embodiment, retraction cord 5 may instead be made substantially wholly of a flexible thermoplastic material 11 (e.g. expanded polytetrafluoroethylene). According to this embodiment, substantially pure PTFE or e-PTFE may be extruded through an injection molding like device of an appropriate diameter so as to form a substantially entirely homogeneous PTFE cord.

Alternatively, a conventional woven or braided retraction cord may be impregnated partially or fully with the non-toxic non-sticking material so as to make up a cord 5 which is both resistant to tearing and to physical attachment or adhesion to dental materials as well as being substantially smooth.

According to yet another embodiment, cord 5 may be made by weaving a plurality of PTFE strands together into a cord-like or tape-like structure.

Flexible cord 5 need not have a substantially circular cross-section. Instead, cord 5 may be tape-like having a substantially rectangular or flat cross-section as illustrated in FIG. 3. Retraction cord or tape 5 as shown in FIG. 3 may include a woven or braided core portion coated with a thermoplastic or alternatively may be made substantially wholly of the thermoplastic material 11 (e.g. expanded PTFE).

FIG. 4 is a side elevational view of the elongated body of retraction cord 5 according to any of the above embodiments. As stated above, the overall length of flexible cord 5 may be determined in accordance with packing and winding requirements as well as with respect to the intended use of the cord.

According to certain other embodiments of this invention, cord 5 may have a triangular, elliptical, or oval cross-section.

Once given the above disclosure, therefore, various other modifications, features, or improvements will become apparent to the skilled artisan. Such other features, modifications, and improvements are thus considered a part of this invention, the scope of which is to be determined by the following claims.

I claim:

1. A flexible dental retraction elongated member of a predetermined size and shape placeable between a tooth and its adjacent gum tissue to properly retract the gum tissue from the tooth a predetermined distance, said dental retraction elongated member being comprised of:

a substantially non-toxic thermoplastic material in an amount sufficient and of a cross-sectional size and shape sufficient to retract the gum tissue, said thermoplastic material being resistant to tearing, shredding, and sticking to dental restorative and impression taking materials.

2. The dental retraction elongated member according to claim 1, wherein said thermoplastic material includes one of polytetrafluoroethylene (PTFE) and e-PTFE.

3. The dental retraction elongated member according to claim 2, wherein said elongated member is in the form of a cord having a substantially circular cross-section, and has an outer diameter of from about 1.0–2.0 mm.

4. The dental retraction elongated member according to claim 2, wherein said elongated member includes a plurality of woven or braided members which are coated with one of said polytetrafluoroethylene and e-PTFE.

5. A dental retraction cord for insertion into the periodontal sulcus between a tooth and its adjacent gum tissue so as to (i) achieve sufficient access to dental caries at, near, or below the gumline; or (ii) retract the gingival tissue prior to and during impression taking procedures for crowns, caps, bridges, dentures, implants, and the like, said dental retraction cord comprising:

an elongated body for insertion into the periodontal sulcus, said elongated body of a cross-sectional size and shape sufficient to retract the gum tissue including a smooth outer surface of a thermoplastic material resistant to shredding, tearing, and adhesion to dental restorative and impression taking materials.

6. The dental retraction cord according to claim 5, wherein said thermoplastic material includes one of PTFE and e-PTFE.

7. The dental retraction cord according to claim 5, wherein said elongated body includes an inner core of a woven or braided material, and wherein said inner core is coated with said thermoplastic material thereby resulting in said smooth outer surface.

8. The dental retraction cord of claim 7, wherein said thermoplastic material includes polytetrafluoroethylene.

9. The dental retraction cord of claim 5, wherein substantially said entire elongated body is made of said thermoplastic material.

10. The dental retraction cord of claim 9, wherein said thermoplastic material includes one of polytetrafluoroethylene (PTFE) and e-PTFE.

11. The dental retraction cord according to claim 5, wherein said elongated body has an outer diameter of from about 0.5–2.5 mm.

12. The dental retraction cord according to claim 11, wherein the outer diameter is from about 1.0–2.0 mm.

13. A method of making and using dental retraction cord for insertion into the periodontal sulcus between a tooth and its adjacent gum, said method comprising the steps of:

a) forming an elongated body for insertion into the periodontal sulcus;

b) including a thermoplastic material in said elongated body; and c) positioning the elongated body including the thermoplastic material in the periodontal sulcus between the tooth and its adjacent gum.

14. The method according to claim 13, wherein said thermoplastic material recited in step b) includes one of polytetrafluoroethylene (PTFE) and e-PTFE.

15. A method of using a thermoplastic dental retraction elongated member including one of PTFE and e-PTFE, the method comprising the steps of:

providing an elongated flexible dental retraction member including one of PTFE and e-PTFE; and placing the elongated flexible member, including one of said PTFE and e-PTFE, between a tooth and its adjacent gum so as to retract gingival tissue.

* * * * *